United States Patent
Dodd et al.

(10) Patent No.: US 6,660,769 B1
(45) Date of Patent: Dec. 9, 2003

(54) N SUBSTITUTED 3-AMINO-2,2-DI-C-ALKYL-1,4-BUTYROLACTONES AND 1,4-THIOBUTYROLACTONES FOR USE AS PROMOTER OF γ-AMINOBUTYRIC ACID ACTIVITY AND FOR TREATING NERVOUS DISORDERS AND PREPARATION METHOD

(75) Inventors: Robert Dodd, Paris (FR); Ahmed El Hadri, Saint-Michel-sur-Orge (FR); Jean-Paul Pierre Potier, Paris (FR); Werner Sieghart, Vienna (AT); Frantisek Jursky, Bratislava (SK); Roman Furtmuller, Pyhra (AT); Erwin Sigel, Bremgarten (CH); Urs Thomet, Hofstetten (CH)

(73) Assignees: Centre National de la Recherche Scientifique (CNRS), Paris (FR); Innovationsagentur GmbH, Vienna (AT); Universite de Bern, Bern (CH)

( * ) Notice: Subject to any disclaimer, the term of this patent is extended or adjusted under 35 U.S.C. 154(b) by 37 days.

(21) Appl. No.: 10/111,091

(22) PCT Filed: Oct. 20, 2000

(86) PCT No.: PCT/FR00/02928

§ 371 (c)(1),
(2), (4) Date: Jun. 26, 2002

(87) PCT Pub. No.: WO01/29017

PCT Pub. Date: Apr. 26, 2001

(30) Foreign Application Priority Data

Oct. 22, 1999 (FR) .............................................. 99 13233

(51) Int. Cl.$^7$ .......................... A61K 31/34; A61K 31/38
(52) U.S. Cl. ...................... 514/472; 514/445; 549/321; 549/68
(58) Field of Search ................... 549/68, 321; 514/445, 514/472

(56) References Cited

U.S. PATENT DOCUMENTS 3,968,233 A * 7/1976 Garzia ........................ 424/279
5,719,057 A     2/1998 Hadingham et al. ........ 435/357

FOREIGN PATENT DOCUMENTS

EP    0 151 964       8/1985
EP      151964 A1 *   8/1985
EP    0 229 007      11/1990

OTHER PUBLICATIONS

Canney et al., "Synthesis and Structure–Activity Studies of Alkyl–substituted gamma–Butyrolactones and gamma–Thiobutyrolactones: Ligands for the Picrotoxin Receptor," *Journal of Medicinal Chemistry* (1991), vol. 34, pp. 1460–1467, XP002146077, Washington US, abstract, p. 1461, col. 2; table III.

Jefford et al., "185.A Practical Synthesis of (2S, 3R)–3–Amino–2–Methylpentanoic Acidfrom L–Aspartic Acid," *Helvetica Chimica ACTA, CH, Verlag Helvetica Chimca ACTA. Basel* (1994), vol. 77, No. 8, pp. 2142–2146, XP002070485, ISSN: 0018–019X, p. 2145; examples 9,10.

W. Sieghart et al., *Affinity of Various Ligands for Benzodiazepine Receptors in Rat Cerebellum and Hippocampus*, Biochemical Pharmacology, vol. 33, No. 24, pp. 4033–4038, 1984, Pergamon Press Ltd.

R. Study et al., *Diazepam and (–)–pentobarbital: Fluctuation analysis reveals different mechanisms for potentiation of γ–aminobutyric acid responses in cultured central neurons*, Neurobiology. vol. 78, No. 11, pp. 7180–7184, Nov. 1981, Proc. Natl. Acad. Sci. USA.

W. Sieghart, *Structure and Pharmacology of γ–Aminobutyric Acid$_A$ Receptor Subtypes*, Pharmacological Reviews, vol. 47, No. 2, 1995, Am. Society for Pharmacology and Experimental Therapeutics.

M. Collis et al., *A Stereodivergent Synthesis of 3,4–Disubstituted–2–Azetidinones*, Tetrahedron: Asymmetry, vol. 7, No. 7, pp. 2117–2134, 1996, Elsevier Science Ltd.

P. Wingrove et al., *The modulatory action of lorecleole at the γ–aminobutyric acid type A receptor is determined by a single amino acid in the $β_2$ and $β_3$ subunit*, Neurobiology, vol. 91, pp. 4569–4573, May 194, Proc. Natl. Acad. Sci. USA.

D. Canney et al., *Synthesis and Structure–Activity Studies of Alkyl–Substituted γ–Butyrolactones and γ–Thiobutyrolactones: Ligands for the Picrotoxin Receptor*, J. Med. Chem., vol. 34, No. 4, pp. 1460–1467, 1991, Am. Chemical Society.

K. Williams et al., *Lactone Modulation of the γ–Aminobutyric AcidA Receptor: Evidence for a Positive Modulatory Site*, Molecular Pharmacology, vol. 52, No. 1, pp. 114–119, 1997, Am. Society for Pharmacology and Experimental Therapeutics.

K. Holland et al., *Alkyl–substituted γ–butyrolactones act at a distinct site allosterically linked to the TBS/picrotoxinin site on the $GABA_A$ receptor complex*, Brain Research, vol. 615, No. 1, pp. 170–174, 1993, Elsevier Science Publishers B.V.

(List continued on next page.)

*Primary Examiner*—Amelia Owens
(74) *Attorney, Agent, or Firm*—Foley & Lardner

(57) ABSTRACT

The invention concerns compounds represented by general formula (I) wherein: Z represents a sulfur or oxygen atom; the groups R1 and R2, identical or different, represent each a alkyl group or an alkenyl group; X represents a CO, a $CO_2$, an SO, or an $SO_2$ and the group R represents an alkyl, aryl, alkenyl, or aralkyl group, provided that when Z represents an oxygen atom, X an $SO_2$ and R a group (a), R1 and R2 do not both represent the methyl group. The invention also concerns methods for preparing said compounds, pharmaceutical compositions containing them and their use as promoter of γ-aminobutyric acid and as medicine particularly designed for treating nervous disorders.

17 Claims, No Drawings

OTHER PUBLICATIONS

G. Dawson et al., *Lack of effect of flumazenil and CGS 8216 on the anxiolytic–like properties of loreclezole*, European Journal of Pharmacology, vol. 252, No. 3, pp. 325–328, 1994, Elsevier–Science B.V.

G. Mathews et al., *Physiological Comparison of α–ethyl–α–methyl–γ–thiobutyrolactone with Benzodiazepine and Barbiturate Modulators of $GABA_A$ Receptors*, Neuropharmacology, vol. 35, No. 2, pp. 123–136, 1996, Elsevier Science Ltd.

S. Arbilla et al., *Pharmacological profile of the imidazopyridine zolpidem at benzodiazepine receptors and electrocorticogram in rats*, Naunyn–Schmiedeberg's Arch. Pharmacol., vol. 330, No. 3, pp. 248–251, 1985, Springer–Verlag.

C. Gardner et al., *The Rapidly Expanding Range Of Neuronal Benzodiazepine Receptor Ligands*, Progress in Neurobiology, vol. 40, No. 1, pp. 1–61, 1993, Pergamon Press Ltd.

J. Zezula et al., *Interaction of allosteric ligands with $GABA_A$ receptors containing one, two, or three different subunits*, European J. of Pharmacology, vol. 301, Nos. 1–3, pp. 207–214, 1996, Elsevier Science B.V.

E. Sigel et al., *The Effect of Subunit Composition of Rat Brain $GABA_A$ Receptors on Channel Function*, Neuron, vol. 5, No. 5, pp. 703–711, Nov. 1990, Cell Press.

A. Wauquier et al., *Loreclezole (R 72 063): An Anticonvulsant Chemically Unrelated to Prototype Antiepileptic Drugs*, Drug Development Research, vol. 19, pp. 375–392, 1990, Wiley–Liss, Inc.

R. Manske, *The Alkaloids Of Fumaraceous Plants II. Dicentra Cucullaria (L.) Bemh*, Can. J. Res., vol. VII, pp. 265–269, 1932, National Research Council of Canada.

P. Krogsgaard–Larsen et al., *$GABA_A$ Receptor Agonists, Partial Agonists, and Antagonists. Design and Therapeutic Prospects*, J. of Medicinal Chemistry, vol. 37, No. 16, pp. 2489–2505, 1994, Am. Chemical Society.

G. McGarvey et al., *L–Aspartic Acid in Acyclic Stereoselective Synthesis. Synthetic Studies on Amphotericin B*, J. Am. Chem. Soc., vol. 108, No. 16, pp. 4943–4952, 1986, Am. Chemical Society.

W. Klunk et al., *Alpha–Substitutted γ–Butyrolactones: New Class of Anticonvulsant Drugs*, Science, vol. 217, pp. 1040–1041, 1982, AAAS.

* cited by examiner

N SUBSTITUTED 3-AMINO-2,2-DI-C-ALKYL-1,4-BUTYROLACTONES AND 1,4-THIOBUTYROLACTONES FOR USE AS PROMOTER OF γ-AMINOBUTYRIC ACID ACTIVITY AND FOR TREATING NERVOUS DISORDERS AND PREPARATION METHOD

This application is a 371 of PCT/FR00/02928 filed Oct. 20, 2000.

The present invention relates to N-substituted 3-amino-2,2-di(C-alkyl)-1,4-butyrolactones and -1,4-thiobutyrolactones, to their preparation, to the pharmaceutical compositions comprising them and to their use as stimulant of the activity of γ-aminobutyric acid and as medicament preferably intended for the treatment of nervous disorders.

The GABA-A Receptor

γ-Aminobutyric acid (or GABA (1)) is the most important inhibitory neurotransmitter of the central nervous system. It acts at the level of three separate classes of receptors known as GABA-A, GABA-B and GABA-C receptors. The GABA-A receptor, the amino acid sequence of which has been determined by cloning techniques, is a pentameric structure composed of α, β, γ, δ and/or ρ subunits. To date, 6 α subunits, 3 β subunits, 3 γ subunits, 1 δ subunit and 2 ρ subunits have been identified and sequenced. Five of these subunits (for example $2\alpha_1 \, 2\beta_2 \, \gamma_2$) combine together to form a channel permeable to chloride ions. By binding to this GABA-A receptor, GABA increases the permeability of the channel to chloride ions, thus inhibiting neuronal transmission. In the light of the large number of possible permutations of the various subunits, the GABA-A receptor is observed to be extremely heterogeneous in the brain of mammals and different structures in the brain generally show a preference for certain combinations of subunits.

The search for ligands which are selective for one of these various subclasses of GABA-A receptors is a major object of clinical medical research in this field.

Apart from GABA, a large number of various classes of compounds which bind to the GABA-A receptor are known. Some products, such as muscimol and isoguvacine, bind directly to the same site as GABA on the GABA-A receptor and stimulate the receptor in the same way as GABA itself. In contrast to these agonists, some substances, such as bicuculline (2), competitively inhibit the action of GABA. Such antagonists of the GABA receptor show convulsant properties in vivo (P. Krogsgaard-Larsen, B. Frolund, F. S. Jorgensen, A. Schousboe, J. Med. Chem., 1994, 37, 2489).

The inhibitory action of GABA can be modulated by compounds which interact with a variety of allosteric sites on the GABA-A receptor distinct from the GABA recognition site. One of the best known classes of allosteric modulators of the GABA-A receptor is that of the benzodiazepines (for example diazepam (3)). By thus binding to their own recognition site on the GABA-A receptor (the benzodiazepine receptor or BZR), these compounds improve the action of GABA by increasing the frequency of opening of the chloride channel (R. E. Study, J. L. Barker, Proc. Natl. Acad. Sci. USA, 1981, 78, 7180). This results in the anticonvulsant, anxiolytic, sedative-hypnotic and muscle-relaxant activities of these products, widely used clinically. Other classes of compounds structurally unrelated to benzodiazepines, such as triazolopyridazines (for example Cl 218872 (4)), imidazopyridines (for example zolpidem (5)), cyclopyrrolones (for example zopicolone (6)) and β-carbolines (for example β-CCM (7)), can also bind to the benzodiazepine receptors. In the case of the latter, some derivatives inhibit, rather than enhance, the neuroinhibitory action of GABA (R. L. Macdonald, R. E. Twyman in "Ion Channels" ed. by T. Narahashi, Vol. 3, pp. 315–343, Plenum Press, New York, 1992). In this case, the compounds, generally convulsant, are referred to as inverse agonists (or negative allosteric modulators) of the BZR, in order to distinguish them from the therapeutically useful agonists (or positive allosteric modulators) of the BZR. Some of these products show selectivity at the level of the various subclasses of GABA-A/benzodiazepine receptors. Thus, zolpidem, used clinically as hypnotic, is selective for the subclass of benzodiazepine receptors which is found predominantly in the cerebellum (BZ1 receptors) (S. Arbilla, H. Depoortere, P. George, S. Z. Langer, Naunyn-Schmiedeberg's Arch. Pharmacol., 1985, 330, 248). This selectivity is reflected either by a narrower spectrum of activity (for example, anxiolysis without a hypnotic effect) or by a reduction in the undesirable effects of this type of product (habituation, dependency, amnesia, and the like).

Other sites exist on the GABA-A receptor which also make it possible, according to the binding of the receptor with an appropriate molecule, to modulate the activity of GABA. Mention should be made, among these sites, of those for neurosteroids (for example 3α-OH-5α-pregnane-20-one), barbiturates (for example pentobarbital), anesthetics (for example propofol), t-butyl-bicyclophosphorothionate cage convulsants (for example TBPS, 8), which bind to the picrotoxin site of the GABA-A receptor (W. Sieghart, Pharmacol. Rev., 1995, 47, 181 and C. R. Gardner, W. R. Tully, C. J. R. Hedgecock, Prog. Neurobiol., 1993, 40, 1). Other binding sites, less well characterized but apparently distinct, are those of loreclezole and of γ-butyrolactones. Such compounds also positively modulate the action of GABA and this effect is reflected by an in vivo anticonvulsant and/or anxiolytic action.

It has recently been demonstrated that gem-dialkylated γ-butyrolactones (9a) and gem-dialkylated γ-thiobutyrolactones (9b) can either reduce or enhance the action of GABA according to the position and the size of their alkyl substituents (K. D. Holland, M. G. Bouley, D. F. Covey, J. A. Ferrendelli, Brain Res., 1993, 615, 170). These compounds allosterically inhibit the binding of $[S^{35}]$TBPS to rat brain membranes but do not displace $[H^3]$-flunitrazepam from its binding site, not enhancing either the binding of benzodiazepines or of muscimol. This suggests that the compounds of type 9 may act on a different site from those already characterized on the GABA-A receptor complex.

Finally, loreclezole (10) is a novel compound which demonstrates both an anticonvulsant activity and an anxiolytic activity in various animal models (A. Wauquier et al., Drug Dev. Res., 1990, 19, 375 and G. R. Dawson, R. Curnow, P. Bayley, A. Rambridge, M. D. Tricklebank, Eur. J. Pharmacol., 1994, 252, 325). These compounds have only a negligible affinity for benzodiazepine recognition sites. Although the direct interaction of loreclezole with GABA-A receptors has been demonstrated in recombinant receptor studies, the relationship between the loreclezole binding sites and the other allosteric binding sites of this receptor is not clear to date. It has recently been demonstrated that the affinity of loreclezole for receptors comprising $\beta_2$ or $\beta_3$ subunits is 300 times greater than that for receptors comprising the $\beta_1$ subunit (P. B. Wingrove, K. A. Wafford, C. Bain, P. J. Whiting, Proc. Natl. Acad. Sci. USA, 1994, 91, 4569). This selectivity may explain the absence of sedative effects of loreclezole and suggests that the compounds interacting with the loreclezole binding site on the GABA-A receptor may have important therapeutic applications.

It is therefore clear that a large number of allosteric modulatory sites, which can enhance the action of GABA and thus show a therapeutic effectiveness in a wide range of disorders of the central nervous system, exist on the GABA-A receptor. It may therefore be reasonably concluded that novel chemical structures may discover other allosteric modulatory sites currently uncharacterized on the GABA-A receptor or may bind to known sites with greater affinities or greater selectivities. Such compounds may, as a result, show a powerful and/or highly specific activity and weaker undesirable side effects in the treatment of such disorders.

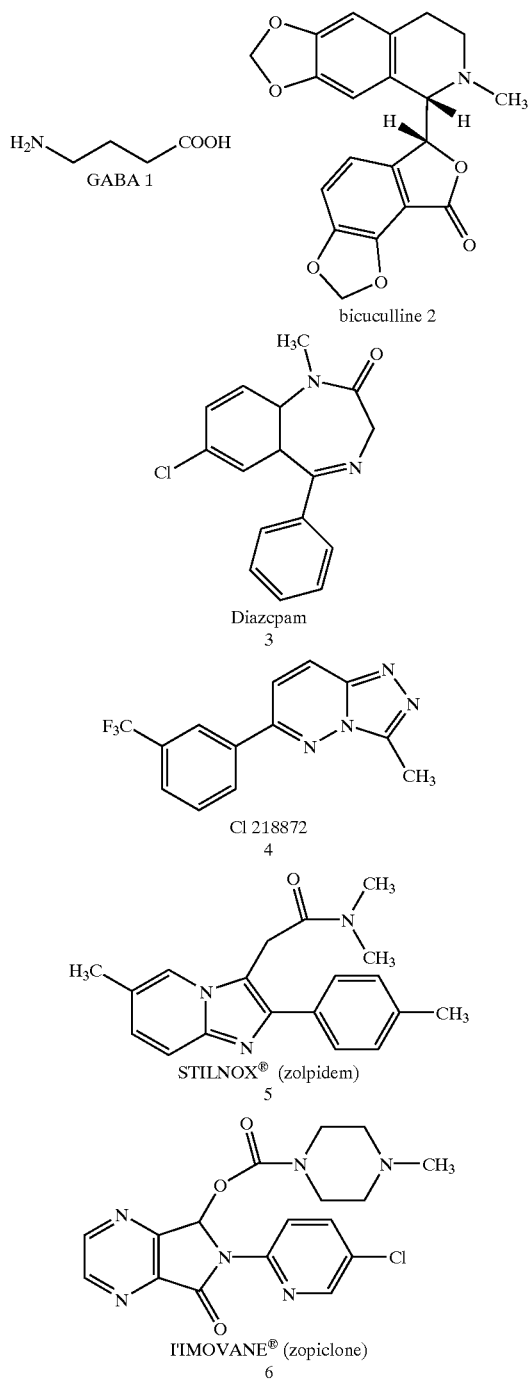

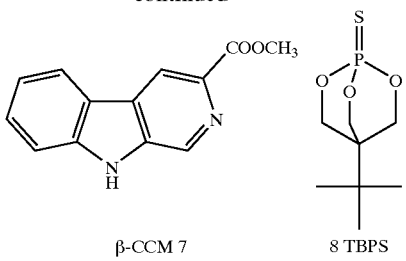

β-CCM 7        8 TBPS

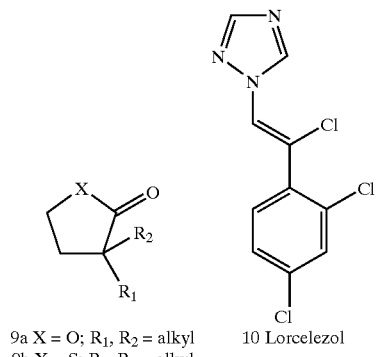

9a X = O; R$_1$, R$_2$ = alkyl    10 Lorcelezol
9b X = S; R$_1$, R$_2$ = alkyl

Covey et al. were the first to indicate the convulsant and anticonvulsant properties of gem-dialkyl-1,4-butyrolactones (W. E. Klunk, A. C. McKeon, D. F. Covey, J. A. Ferrendelli, Science, 1982, 217, 1040). They found that, whereas dialkyl substitutions in the β (that is to say C-3) position of butyrolactone (for example compound 54) produces convulsant effects in mice, similar substituents in the α (that is to say C-2) position (for example compound 55) lead to compounds having anticonvulsant properties in mice, preventing the attacks induced by pentylenetetrazole and picrotoxin. Structure-function studies on compound 55 indicated that the anticonvulsant activity was maintained as long as the alkyl substituents comprised 4 carbon atoms or less. If more carbon atoms were present, convulsant effects were observed. These authors also studied α-alkyl substituted -1,4-thiobutyrolactones (for example 48, α-EMTBL) (D. F. Covey et al., J. Med. Chem., 1991, 34, 1460), cyclopentanones 56 and lactams (for example 57). Likewise, anticonvulsant activities were observed in these three series of compounds with short-chain alkyl substituents.

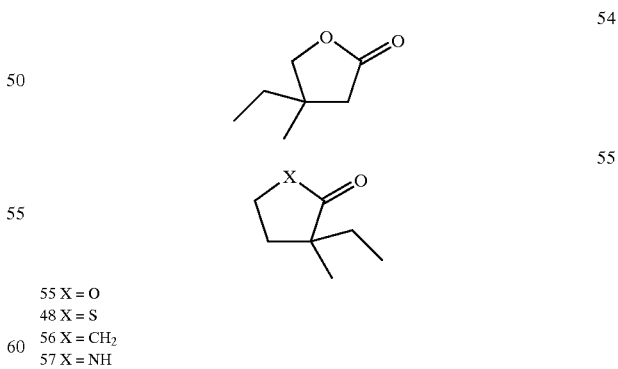

55 X = O
48 X = S
56 X = CH$_2$
57 X = NH

In vitro data for the most active examples of these compounds in their ability to displace S$^{35}$-TBPS (indicating an affinity with the picrotoxin binding site of the GABA-A receptor) and their ability to stimulate currents produced by GABA in cultured neurons are shown in table 5.

TABLE 5

Displacement of TBPS and potentiation of GABA produced by various published compounds related to those of the present invention.

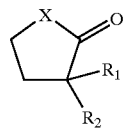

| Compounds | X | $R_1$ | $R_2$ | Displacement of $S^{35}$-TBPS ($IC_{50}$) | % of stimulation of GABA (concentration) |
|---|---|---|---|---|---|
| 55 | O | Et | Me | 2.3 mM | +101 ± 8 (300 µM) |
| 48 | S | Et | Me | 0.33 mM | +176 ± 10 (300 µM) |
| 58 | NH | Et | Et | 5.8 mM | +137 ± 6 (1 µM) |
| 59 | NH | Bn | Et | 0.44 mM | +136 ± 8 (300 µM) |
| 56 | $CH_2$ | Et | H | 2.4 mM | — |
| 60 | S | $CF_3CH_2$ | Me | 0.52 mM | +160 ± 17 (300 µM) |
| 61 | O | $CF_3CH_2$ | Me | 3.1 mM | +146 ± 12 (1 µM) |

The most active compounds of the invention (30, 31, 34, 35) are generally more powerful in displacing TBPS (see tables 2a and 2b) than the published compounds shown in table 5. More importantly, the active compounds of the invention are more powerful in stimulating the currents produced by GABA. Thus, whereas the percentage of stimulation of GABA currents by relatively high concentrations (0.3–1 mM) of the published compounds were invariably less than +200%, the compounds of the present invention stimulate the GABA response by up to +700%, this being achieved at lower concentrations (100 µM).

The observation that there is very little correlation between the TBPS displacement capacities and the GABA potentiation (and with the anticonvulsant capacity) led Covey et al. to suggest that the compounds of this family (in particular α-EMTBL, 48, on which the largest number of studies have been carried out) act partially by binding to a site at or close to the picrotoxin site of the GABA-A receptor, as well as to a separate site of the receptor specific to lactones and thiolactones (the butyrolactone site) (D. F. Covey et al., Mol. Pharmacol., 1997, 52, 114). It has been demonstrated that these compounds do not bind to the barbiturate and benzodiazepine binding site of the GABA-A receptor (D. F. Covey et al., Neuropharmacology, 1996, 35, 123).

On the other hand, there has been no suggestion or indication in the literature that dialkyl-1,4-butyrolactones and -thiobutyrolactones interact with the anticonvulsant loreclezole (10) recognition site of the GABA-A receptor. Indirect evidence suggests that this is not the case since α-EMTBL (48) stimulates GABA-A receptors composed only of α subunits (D. F. Covey et al., Neuropharmacology, 1996, 35, 123), whereas it is known that the loreclezole binding site is present only on receptors comprising $β_2$ and $β_3$ subunits (P. B. Wingrove, K. A. Wafford, C. Bain, P. J. Whiting, Proc. Natl. Acad. Sci. USA, 1994, 91, 4569).

It is thus apparent that the presence of a substituted amine functional group in the C-3 position of 2,2-dialkyl-1,4-butyrolactones, a subject matter of the present invention, leads to a greater enhancement in the GABA effects than the analogous molecules described which do not have this functionality. It is also apparent that, at least in some cases, some of the compounds of the invention can act via the new loreclezole binding site on the GABA-A receptor. These two properties give the compounds of the invention a potentially high therapeutic value.

The present invention thus relates to the compounds of general formula:

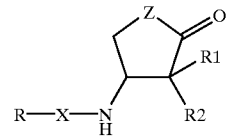

in which:

Z represents a sulfur or oxygen atom, the R1 and R2 groups, which can be identical to or different from one another, each represent an alkyl group or an alkenyl group, X represents a CO, a $CO_2$, an SO or an $SO_2$, and the R group represents an alkyl, aryl, alkenyl or aralkyl group, provided that, when Z represents an oxygen atom, X an $SO_2$ and R a

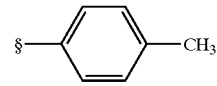

group,

R1 and R2 do not both represent the methyl group.

The preferred compounds of the present invention are such that Z represents an oxygen atom. This is because they have a more advantageous activity.

A specific group of compounds according to the invention is composed of the compounds of general formula:

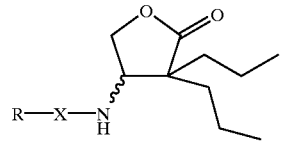

in which:

X represents a CO, a $CO_2$, an SO or an $SO_2$, and the R group represents an alkyl, aryl, alkenyl or aralkyl group.

Mention may be made, among the preferred compounds of the invention, of the compound of formula:

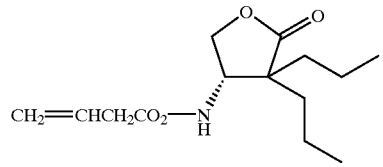

The term "alkyl group" is understood to denote linear or branched and substituted or unsubstituted alkyl groups comprising 1 to 8 carbon atoms. Preferred examples of alkyl groups are the $CH_3$, $CH_2CH_3$, $CH_2CH_2CH_3$ and $C(CH_3)_3$ groups.

The term "alkenyl group", is understood to mean linear or branched and substituted or unsubstituted alkenyl groups comprising 1 to 6 carbon atoms. A preferred example of alkenyl groups is $CH_2CH=CH_2$.

The term "aryl groups" is understood to mean substituted or unsubstituted aromatic rings having at least 3 carbon atoms which have just one or several aromatic nucleus. The aromatic rings can be fused. Examples of preferred aromatic rings are phenyls and naphthyls. Examples of preferred substituents of these rings are alkyl groups, such as $CH_3$, halogen atoms, such as Cl, halogenated alkyl groups, such as $CF_3$, groups of the $OCH_3$ type and amines, such as $NH_2$ or $N(CH_3)_2$.

The term "aralkyl groups" is understood to mean aryl groups, defined as above, bonded to the CO or SO or $CO_2$ or $SO_2$ group via an alkyl group defined as above. A preferred example of an aralkyl group is the $CH_2Ph$ group.

The compounds according to the invention all have a center of asymmetry and can therefore exist in the form of optical isomers. The present invention equally well comprises these isomers, either separately or as a mixture.

The present invention also relates to the method of preparation of the compounds of following general formula I:

in which:
Z represents a sulfur or oxygen atom,
the R1 and R2 groups, which can be identical to or different from one another, each represent an alkyl group or an alkenyl group,
X represents a CO, a $CO_2$, an SO or an $SO_2$,
and the R group represents an alkyl, aryl, alkenyl or aralkyl group,
which can be as follows:
the amine of the compound of general formula:

in which:
Z represents a sulfur or oxygen atom, preferably an oxygen atom,
and the R1 and R2 groups, which can be identical to or different from one another, each represent an alkyl group or an alkenyl group,
is treated with an appropriate reactant in order to obtain the compounds according to the present invention. Preferably, this reactant is one of the family of the acyl chlorides, sulfonyl chlorides or chloroformates.

This process can comprise a preliminary stage of hydrogenolysis in order to remove the benzyl group from the compound of general formula:

in which:
Z represents a sulfur or oxygen atom, preferably an oxygen atom,
and the R1 and R2 groups, which can be identical to or different from one another, each represent an alkyl group or an alkenyl group.

This stage can be preceded by a stage of alkylation in the C-2 position of the compound of general formula:

in which:
z represents a sulfur or oxygen atom, preferably an oxygen atom,
and the R1 group represents an alkyl group or an alkenyl group,
by treatment with a strong base, followed by the addition of an alkylating agent of general formula R2X in which R2 represents an alkyl, alkenyl or aralkyl group.

This stage can also be preceded by a stage of monoalkylation in the C-2 position of the 3-benzyl-aminolactone of general formula:

in which:
Z represents a sulfur or oxygen atom, preferably an oxygen atom,
by treatment with a strong base, followed by the addition of an alkylating agent of general formula R1X in which R1 represents an alkyl, alkenyl or aralkyl group.

This stage can also be preceded by a stage of 1,4 addition of Michael type of benzylamine to an unsaturated 1,4-butyrolactone or 1,4-thiobutyrolactone to give the corresponding 3-benzylaminolactone.

In a preferred preparation process according to the present invention, the starting material which makes it possible to obtain, as in the preceding stage, the corresponding optically pure 3-benzylaminolactone is a D- or L-aspartic acid. The compounds obtained at the end of this process, after the 5 stages described above, are then optically pure.

In another preparation process example, the strong base used to carry out the alkylations is lithium hexamethyldisilazide.

The present invention also relates to pharmaceutical compositions comprising, as active principle, a compound of following general formula:

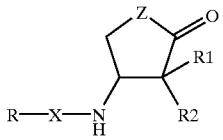

in which:
Z represents a sulfur or oxygen atom,
the R1 and R2 groups, which can be identical to or different from one another, each represent an alkyl group or an alkenyl group,
X represents a CO, a $CO_2$, an SO or an $SO_2$,
and the R group represents an alkyl, aryl, alkenyl or aralkyl group,
and an appropriate excipient. These compositions can be formulated for administration to mammals, including man. The dosage varies according to the treatment and according to the ailment in question. These compositions are produced so as to be able to be administered by the digestive or parenteral route.

In the pharmaceutical compositions of the present invention for oral, sublingual, subcutaneous, intramuscular, intravenous, transdermal, local or rectal administration, the active ingredient can be administered in unit administration forms, as a mixture with conventional pharmaceutical carriers, to animals or human beings. The appropriate unit administration forms comprise oral forms, such as tablets, gelatin capsules, powders, granules and oral solutions or suspensions, sublingual and buccal administration forms, subcutaneous, intramuscular, intravenous, intranasal or intraocular administration forms and rectal administration forms.

When a solid composition is prepared in the form of tablets, the main active ingredient is mixed with a pharmaceutical vehicle, such as gelatin, starch, lactose, magnesium stearate, talc, gum arabic or similar materials. The tablets can be coated with sucrose or with other appropriate materials or they can be treated so that they have a prolonged or delayed activity and so that they continuously release a predetermined amount of active principle.

A preparation in gelatin capsules is obtained by mixing the active ingredient with a diluent and by pouring the mixture obtained into soft or hard gelatin capsules.

A preparation in the syrup or elixir form can comprise the active ingredient in conjunction with a sweetener, an antiseptic, and a flavor enhancer and an appropriate dye.

The water-dispersible powders or granules can comprise the active ingredient as a mixture with dispersing agents or wetting agents, or suspending agents, and with flavor enhancers or sweeteners.

For rectal administration, recourse is had to suppositories which are prepared with binders which melt at the rectal temperature, for example cocoa butter or polyethylene glycols.

For parenteral, intranasal or intraocular administration, use is made of aqueous suspensions, isotonic saline solutions or sterile injectable solutions which comprise pharmacologically compatible dispersing agents and/or wetting agents.

The active principle can also be formulated in the form of microcapsules, optionally with one or more additional carriers.

The present invention also relates to the use of the compounds of following general formula:

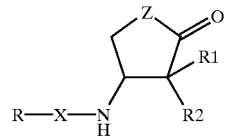

in which:
Z represents a sulfur or oxygen atom,
the R1 and R2 groups, which can be identical to or different from one another, each represent an alkyl group or an alkenyl group,
X represents a CO, a $CO_2$, an SO or an $SO_2$, and the R group represents an alkyl, aryl, alkenyl or aralkyl group,
as stimulant of the activity of γ-aminobutyric acid acting via the GABA-A receptor of the central nervous system.

The compounds according to the invention of following general formula:

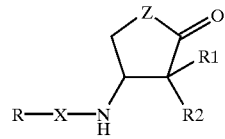

in which:
Z represents a sulfur or oxygen atom, the R1 and R2 groups, which can be identical to or different from one another, each represent an alkyl group or an alkenyl group,
X represents a CO, a $CO_2$, an SO or an $SO_2$,
and the R group represents an alkyl, aryl, alkenyl or aralkyl group,
and the pharmaceutical compositions comprising them can be used as a medicament, in particular for the treatment of nervous disorders. These disorders are preferably of the following types: epilepsy, anxiety, depression, sleep disorders, panic attacks, muscular contractions, pain, dependence on alcohol or benzodiazepines, or psychotic behaviors.

PREPARATION OF THE RACEMIC COMPOUNDS

Using the method described by Perlmutter (M. P. Collis, P. Perlmutter, Tetrahedron: Asymmetry, 1996, 7, 2117), the 1,4 addition of Michael type of benzylamine to commercial 2(5H)-furanone 12 in methanol gives a racemic mixture of 3-benzylamino-1,4-butyrolactone 13 (scheme 1). The latter is treated first of all with lithium hexamethyldisilazide in THF at −78° C. and subsequently with an alkyl halide in the presence of HMPA, to give the cis/trans mixture of the 2-monoalkyl-3-benzylamino-1,4-butyrolactone 14, which can be separated by a chromatographic column on silica gel. Methyl iodide, p-methoxybenzyl chloride and 2-bromoethylbenzene are used as typical alkylating agents.

In the case of allyl bromide, the main product obtained is the 2,2-diallyl derivative 16. The monoalkyl derivatives 14 can later be alkylated to asymmetric 2,2-dialkylated derivatives 15.

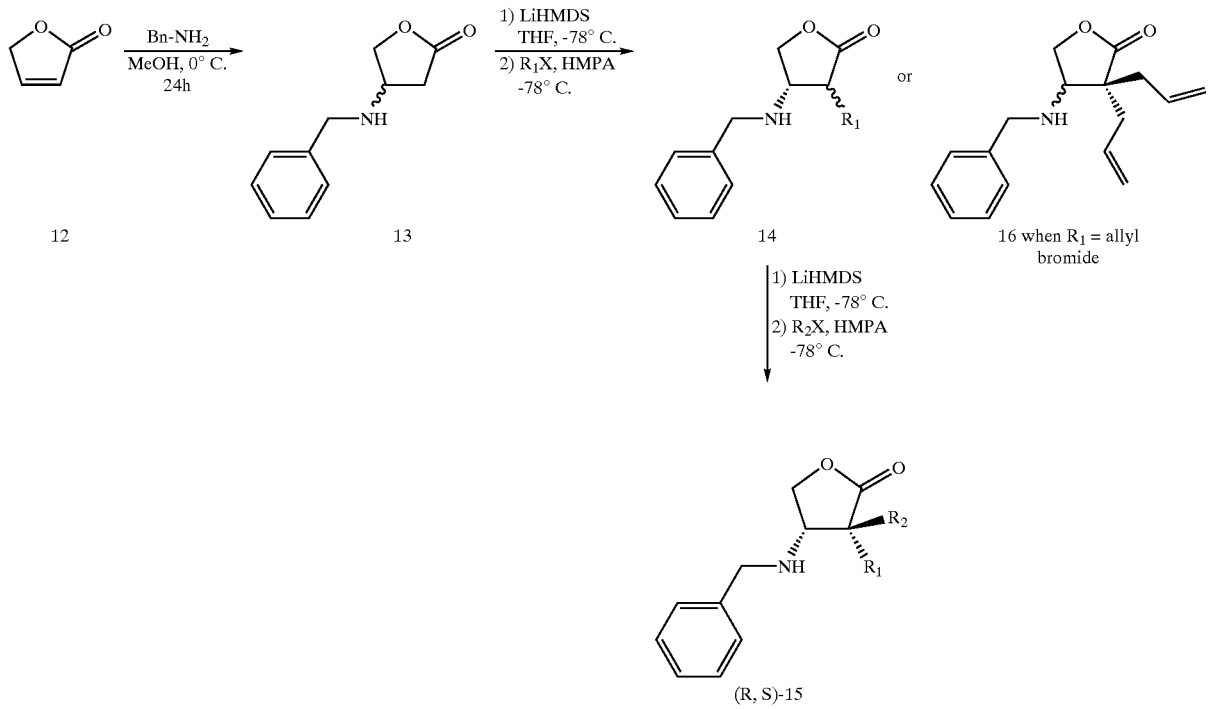

Scheme 1

The monoalkylated derivatives 14 or dialkylated derivatives are subjected to catalytic hydrogenolysis in ethanol at 40 psi in the presence of 10% palladium-on-carbon to give the corresponding unstable 3-amino derivatives 17 or 18 respectively (scheme 2). The latter are immediately treated in dichloromethane in the presence of triethylamine and DMAP with alkyl, alkenyl or arylsulfonyl chlorides, alkyloxycarbonyl, alkenoxycarbonyl or aryloxycarbonyl chlorides or alkyl, alkenyl or aryl acid chlorides to give the corresponding N-substituted derivatives 19 or 20 respectively. Alternatively, the compounds 14 or 15 can be treated with the same reactants to give the N,N-disubstituted derivatives 21 or 22 respectively.

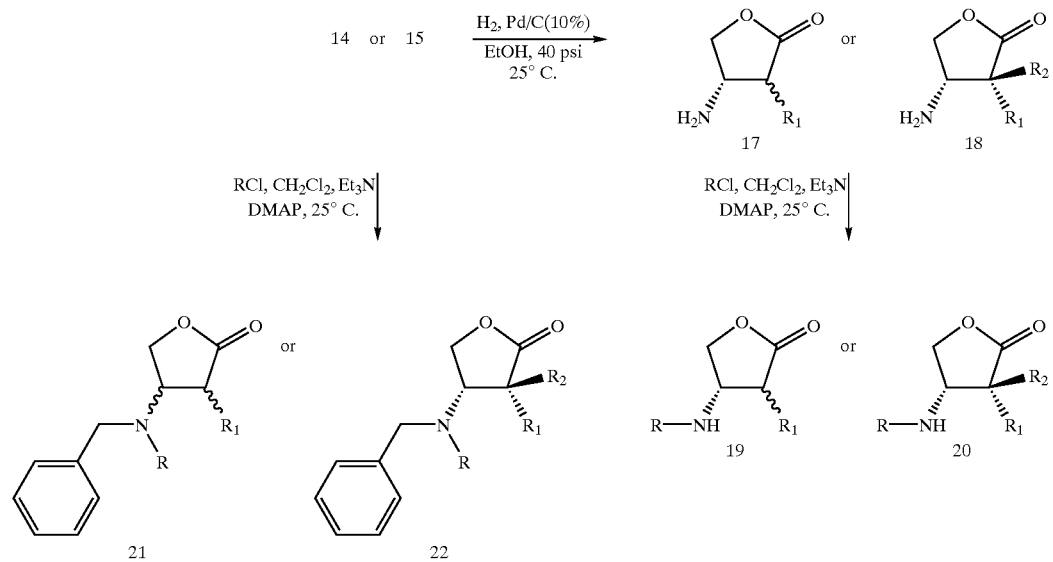

Scheme 2

In the special case of the diallyl derivative 16, the hydrogenolysis of the N-benzyl group also leads to the reduction of the double bonds to give 2,2-dipropyl-3-amino-1,4-butyrolactone 18 (R1=R2=propyl), which is sulfonylated or N-acylated as above to give the compounds 20 (R1=R2=propyl).

Scheme 3

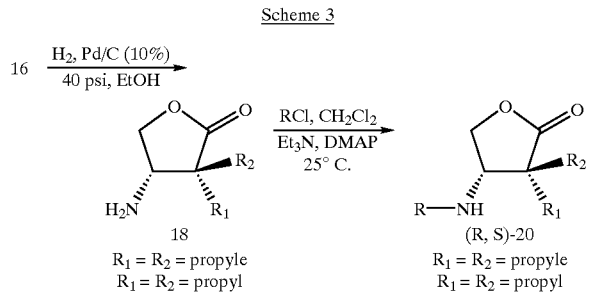

Isolation of the Pure Enantiomers of the Compounds According to the Invention a) By HPLC on a Chiral Column The racemic mixtures of the compounds R,S-20 can be separated by HPLC on a chiral column. For example, the application of 40 mg of the racemate 30 to a chiral OD column and the elution with 9:1 hexane/2-propanol results in the isolation of 12 mg of R isomer (retention time=12.3 min; $[\alpha]_D$=0.28 (CHCl$_3$)) and of 13 mg of S isomer (retention time=13.6 min; $[\alpha]_D$+0.24 (CHCl$_3$)), the two fractions having an enantiomeric purity of more than 95%.

b) By Enantiospecific Synthesis from Aspartic Acid

The starting 3-benzylamino-1,4-butyrolactone 13 can be prepared in an enantiomerically pure form by starting from L- or D-aspartic acid and by employing a methodology described previously (G. J. McGarvey et al., J. Amer. Chem. Soc., 1986, 108, 4943). Thus, the treatment of D-aspartic acid D-23 in a mixture of ether and 3N sodium hydroxide with benzyloxycarbonyl chloride gives the N-benzyloxycarbonyl derivative 24 (scheme 4). The treatment of the latter with acetic anhydride produces the anhydride 25, which is selectively reduced to (R)-3-(benzyloxycarbonylamino)-1,4-butyrolactone ((R)-26). The removal of the Cbz blocking group by hydrogenolysis and the reductive alkylation of the resulting amine with benzaldehyde gives the benzylamine (R)-13. The treatment of the latter as above with lithium hexamethyldisilazide and an excess of allyl bromide (scheme 1) then gives the compound (R)-16, which can be converted to the compound (R)-20 by using the same series of reactions used to prepare the racemic compound 20 (scheme 3).

Scheme 4

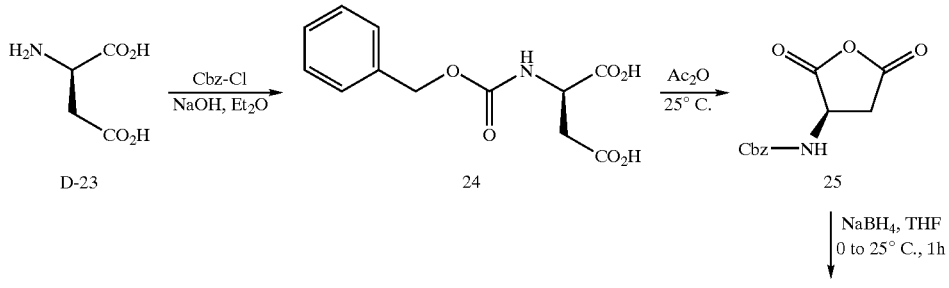

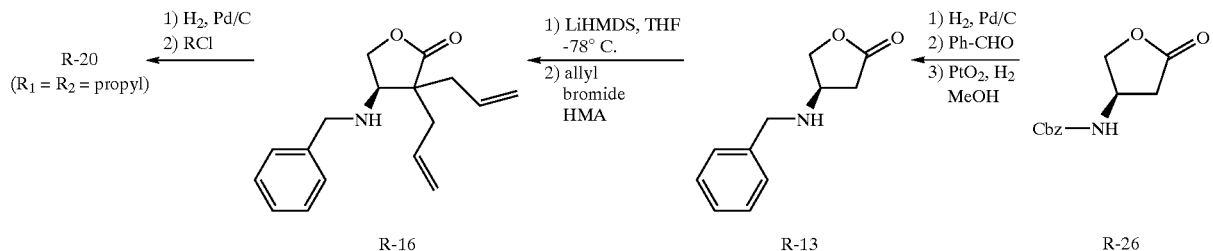

The application of this reaction scheme to L-aspartic acid (L-23) then gives access to the enantiomer (S)-20 (scheme 5).

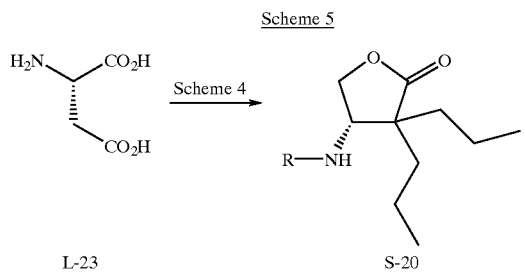

Scheme 5

L-23          S-20

Studies of Binding to the Receptor

The synthesized compounds are tested in vitro for their ability to bind to various sites on the GABA-A receptor, including the GABA site itself (by $H^3$-muscimol displacement studies), the benzodiazepine site (by $H^3$-flunitrazepam displacement) and the picrotoxin site (by $S^{35}$-TBPS displacement). Briefly, frozen membranes originating from the cerebellum or from the cerebellum-free brain are defrosted, centrifuged and suspended in 50 mM of Tris-citrate buffer, pH 7.4, at a protein concentration of approximately 1 mg/ml. The membranes (0.5 ml) are then incubated in a total of 1 ml of solution comprising 50 mM of Tris-citrate buffer, pH 7.4, 150 mM of NaCl and 2 nM of [$H^3$]flunitrazepam or 2 nM of [$H^3$]muscimol in the absence or in the presence of various concentrations of the compound to be studied or of 10 μM of diazepam or 10 μM of GABA, for 90 min at 4° C., respectively. For the [$S^{35}$]TBPS binding, the membranes are incubated in a total of 1 ml of solution comprising 50 mM of Tris-citrate buffer, pH 7.4, 200 mM of NaBr and 2 nM of [$S^{35}$]TBPS in the absence or in the presence of various concentrations of the compound to be studied or of 10 μM of TBPS or of picrotoxinin for 180 min at ambient temperature (W. Sieghart, A. Schuster, Biochem. Pharmacol., 1984, 33, 4033 and J. Zezula et al., Eur. J. Pharmacol., 1996, 301, 207).

The membranes are then filtered through Whatman GF/B filters. When the binding of [$H^3$]flunitrazepam or of [$H^3$] muscimol is studied, the filters are rinsed twice with 5 ml of a buffer solution of 50 mM of ice-cold Tris-citrate. When the binding of [$S^{35}$]TBPS is studied, the filters are rinsed three times with 3.5 ml of this buffer solution. The filters are transferred into scintillation vials and subjected to scintillation counting after addition of 3.5 ml of scintillation fluid. The nonspecific binding, determined in the presence of 10 μM of diazepam, of 10 μM of GABA or of 10 μM of TBPS, is subtracted from the total of the binding of [$H^3$] flunitrazepam, of [$H^3$]muscimol or of [$S^{35}$]TBPS respectively in order to obtain the specific binding.

Electrophysiological Studies

The compounds synthesized are also studied for their ability to cause opening of the channel of the GABA-A receptor or to allosterically modulate the currents caused by GABA. For this purpose, the GABA-A recombinant receptors are expressed in Xenopus oocytes. Briefly, Xenopus laevis oocytes are prepared, injected and defolliculated and the currents are recorded in the way described (E. Sigel, J. Physiol., 1987, 386, 73 and E. Sigel, R. Baur, G. Trube, H. Möhler, P. Malherbe, Neuron, 1990, 5, 703). The oocytes are injected with 50 nl of cRNA dissolved in 5 mM of K-Hepes (pH 6.8). This solution comprises the transcripts coding for the various subunits at a concentration of 10 nM for $\alpha_1$, 10 nM for $\beta_2$ and 50 nM for $\gamma_2$. The RNA transcripts are synthesized from linearized plasmids encoding the desired protein using the message machine kit (Ambion) according to the recommendations of the manufacturers. A poly(A) tail of approximately 300 residues is added to the transcripts using yeast poly(A) polymerase (USB or Amersham). The cRNA combinations are coprecipitated from ethanol and stored at −20° C. The transcripts are quantified on agarose gels, after having been stained with the RNA stain Radiant Red (Bio-Rad), by comparing the intensities of the stainings with various amounts of molecular weight markers (RNA-Ladder, Gibco-BRL). The electrophysiological experiments are carried out by the two-electrode voltage clamp method at a holding potential of −80 mV. The medium comprises 90 mM of NaCl, 1 mM of KCl, 1 mM of $MgCl_2$, 1 mM of $CaCl_2$ and 10 mM of Na-Hepes (pH 7.4). GABA is applied for 20 s and a washing period of 4 min is allowed in order to provide for the complete reestablishment of desensitization. The perfusion system is cleaned between the applications of the compounds by washing with dimethyl sulfoxide to prevent contamination. The compounds are applied at a concentration of 100 microM in the absence of GABA in order to see whether they can act as channel agonists. To study the allosteric modulation, GABA is first of all applied alone and then in combination with either 0.1 microM or 100 microM of compounds.

Pharmacological Results

All the compounds synthesized are tested in vitro for their ability to displace tritiated flunitrazepam ($H^3$-Flu, ligand selective for the benzodiazepine binding site of the GABA-A receptor), $S^{35}$-TBPS (selective for the picrotoxin binding site) and tritiated muscimol (selective for the GABA binding site). These compounds are also tested for their ability to prevent or to stimulate the currents caused by GABA in frog oocytes expressing the $\alpha_1\beta_2\gamma_2$ subtype of the GABA receptor. The detailed results for all the compounds are shown in tables 1a, 1b, 1c and 1d.

TABLE 1a

Percentage of stimulation of the currents produced by GABA by the lactone derivatives in frog oocytes expressing the α1β2γ2 recombinant GABA-A receptors and their displacement of the radiolabeled ligands

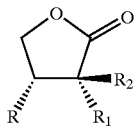

| Cp | R | $R_1$ | $R_2$ | % of stimulation of the GABA currents (200 μM) | % Flu (100 μM) | % TBPS (100 μM) | % Muscimol (100 μM) |
|---|---|---|---|---|---|---|---|
| | | | | | | Inhibition of the radiolabeled ligands | |
| 26 (EA5) | $NHCO_2CH_2Ph$ | H | H | +47 ± 90 (0.1 μM) | 0 | 0 | 0 |
| 27 (EA9c) | $NHCO_2CH_2Ph$ | $CH_3$ | H | −1 ± 2 (50 μM) | 0 | 0 | 10% stimulation |
| 28 (EA9t) | $NHCO_2CH_2Ph$ | H | $CH_3$ | −7 ± 7 (50 μM) | 0 | 0 | 0 |
| 29 (EA22) | H | $CH_2CH_2CH_3$ | $CH_2CH_2CH_3$ | +33 ± 17 (100 μM; α1β1) +60 ± 12 (100 μM; α2β2) +158 ± 79 (400 μM; α1β1) +254 ± 115 (400 μM; α2β2) | 0 | 0 | 0 |

Flu: $H^3$-Flunitrazepam
μM: micromolar
TBPS: $S^{35}$-t-butyl-bicyclophosphorothionate
Muscimol: $H^3$-Muscimol
NT: not tested TABLE 1b

| Cp | R | $R_1$ | $R_2$ | % of stimulation of the GABA currents (200 μM) | % Flu (100 μM) | % TBPS (100 μM) | % Muscimol (100 μM) |
|---|---|---|---|---|---|---|---|
| | | | | | | Inhibition of the radiolabeled ligands | |
| 30 (EA18) | $NH—CO_2CH_2Ph$ | $CH_2CH_2CH_3$ | $CH_2CH_2CH_3$ | +51 ± 30 +250 (50 μM) +140 ± 57 (10 μM) +15 ± 3 (1 μM) | 0 | 55% 0 10 μM | 0 |
| 31 (EA31) | $NH—SO_2Ph\text{-}p\text{-}Cl$ | $CH_2CH_2CH_3$ | $CH_2CH_2CH_3$ | +23 ± 8 (5 μM) (insoluble at >5 μM) | 25% stimulation | $IC_{50}$ = 10 μM | 0 |
| 32 (EA32) | $NH—SO_2Ph\text{-}p\text{-}CF_3$ | $CH_2CH_2CH_3$ | $CH_2CH_2CH_3$ | N.T. | 15–20% stimulation | 100% (10 μM, anterior part of the brain) incomplete inhibition in the cerebellum | 0 |
| 33 (EA33) | $NH—SO_2Ph\text{-}p\text{-}OCH_3$ | $CH_2CH_2CH_3$ | $CH_2CH_2CH_3$ | N.T. | weak stimulation | $IC_{50}$ = 50 μM (cooperativity) | 0 |

TABLE 1b-continued

| Cp | R | $R_1$ | $R_2$ | % of stimulation of the GABA currents (200 μM) | % Flu (100 μM) | % TBPS (100 μM) | % Muscimol (100 μM) |
|---|---|---|---|---|---|---|---|
| | | | | | Inhibition of the radiolabeled ligands | | |
| 34 (EA34) | NH—CO-Ph | $CH_2CH_2CH_3$ | $CH_2CH_2CH_3$ | +420 ± 33 +207 ± 17 (20 μM) +17 ± 3 (2 μM) | weak stimulation | $IC_{50}$ = 100 μM (cooperativity) | 0 |

TABLE 1c

| Cp | R | $R_1$ | $R_2$ | % of stimulation of the GABA currents (200 μM) | % Flu (100 μM) | % TBPS (100 μM) | % Muscimol (100 μM) |
|---|---|---|---|---|---|---|---|
| | | | | | Inhibition of the radiolabeled ligands | | |
| 35 (EA35) | NH—CO—$OCH_2$—H=$CH_3$ | $CH_2CH_2CH_3$ | $CH_2CH_2CH_3$ | +765 ± 61 +229 ± 14 (20 μM) +26 ± 5 (2 μM) | weak stimulation | $IC_{50}$ = 100 μM (cooperativity) | 0 |
| 36 (EA36) | NH—CO—$OCH_2$—$CH_3$ | $CH_2CH_2CH_3$ | $CH_2CH_2CH_3$ | NT | 0 | $IC_{50}$ > 100 μM | 0 |
| 37 (EA44) | NH—$CO_2C(CH_3)_3$ | $CH_2CH_2CH_3$ | $CH_2CH_2CH_3$ | NT | | | |
| 16 (EA17) | NH—$CH_2Ph$ | $CH_2CH=CH_2$ | $CH_2CH=CH_2$ | +115 ± 30 | 10% stimulation | 62% | |
| 38 (EA20c) | NH—$CH_2Ph$ | $CH_2CH_2Ph$ | H | NT | | | |
| 39 (EA20t) | NH—$CH_2Ph$ | H | $CH_2CH_2Ph$ | NT | | | |
| 40 (EA19a) | NH—$CH_2Ph$ | $CH_3$ | $CH_2Ph$-p-$OCH_3$ | NT | | | |
| 41 (EA19b) | NH—$CH_2Ph$ | $CH_2Ph$-p-$OCH_3$ | $CH_3$ | NT | | | |
| 42 (EA12t) | N—($CH_2Ph$)-CO—$OCH_2Ph$ | H | $CH_3$ | +3 ± 10 | 0 | 52% 15% (10 μM) | |

TABLE 1d

| Cp | R | $R_1$ | $R_2$ | % of stimulation of the GABA currents (200 μM) | % Flu (100 μM) | % TBPS (100 μM) | % Muscimol (100 μM) |
|---|---|---|---|---|---|---|---|
| | | | | | Inhibition of the radiolabeled ligands | | |
| 43 (EA12c) | N($CH_2Ph$)-CO—$OCH_2Ph$ | $CH_3$ | H | −3 ± 3 | 30% 20% (10 μM) | 60% 35% (10 μM) | 0 |
| 44 (EA56) | NH—$SO_2$-Ph-p-$NH_2$ | $CH_2CH_2CH_3$ | $CH_2CH_2CH_3$ | | | | |
| 45 (EA54) | NH—$SO_2$-Ph-p-NHY(Y=$CO_2CH_2$—CH=$CH_2$) | $CH_2CH_2CH_3$ | $CH_2CH_2CH_3$ | | | | |
| 46 (EA58) | $NHSO_2$—N($CH_3$)$_2$ | $CH_2CH_2CH_3$ | $CH_2CH_2CH_3$ | | | | |
| 47 (EA57) | NH—$SO_2$-(2-thiophene) | $CH_2CH_2CH_3$ | $CH_2CH_2CH_3$ | | | | |
| 48 (EA46) | α-Ethyl-α-methyl-γ-thiobutyrolactone (EMTBL) | | | | | | |

The most active compounds are summarized in tables 2a and 2b.

TABLE 2a

Activities of certain compounds (racemic mixture) according to the invention on the GABA-A receptor

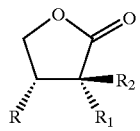

| Cp No. | R | $R_1$ | $R_2$ | % of stimulation of the GABA currents (200 $\mu$M) ($\alpha 1\beta 2\gamma 2$) | % of inhibition of [$^3$H]flunitrazepam (100 $\mu$M) | % of inhibition of [$^{35}$S]TBPS (100 $\mu$M) |
|---|---|---|---|---|---|---|
| 16 | NHCH$_2$Ph | CH$_2$CH=CH$_2$ | H$_2$CH=CH$_2$ | +115 ± 30 | 10% stimulation | 62% |
| 26 | HCO$_2$CH$_2$Ph | H | H | +47 ± 9 | 0 | 0 |
| 29 | H | CH$_2$CH$_2$CH$_3$ | H$_2$CH$_2$CH$_3$ | +33 ± 17 (100 $\mu$M; $\alpha 1\beta 1$) +60 ± 12 (100 $\mu$M; $\alpha 2\beta 2$) +158 ± 79 (400 $\mu$M; $\alpha 1\beta 1$) +254 ± 115 (400 $\mu$M; $\alpha 2\beta 2$) | 0 | 0 |
| 28 | HCO$_2$CH$_2$Ph | H | CH$_3$ | −7 ± 7 (50 $\mu$M) | | |
| 30 | HCO$_2$CH$_2$Ph | CH$_2$CH$_2$CH$_3$ | H$_2$CH$_2$CH$_3$ | +51 ± 30 +250 (50 $\mu$M) +140 ± 57 (10 $\mu$M) +15 ± 3 (1 $\mu$M) | 0 | 55% |
| 31 | NHSO$_2$-Ph-p-Cl | CH$_2$CH$_2$CH$_3$ | H$_2$CH$_2$CH$_3$ | +23 ± 8 (5 $\mu$M) | 25% stimulation | IC$_{50}$ ~10 $\mu$M |

TABLE 2b

| Cp No. | R | $R_1$ | $R_2$ | % of stimulation of the GABA currents (200 $\mu$M) ($\alpha 1\beta 2\gamma 2$) | % of inhibition of [$^3$H]fluni-trazepam (100 $\mu$M) | % of inhibition of [$^{35}$S]TBPS (100 $\mu$M) |
|---|---|---|---|---|---|---|
| 34 | NHCOPh | CH$_2$CH$_2$CH$_3$ | H$_2$CH$_2$CH$_3$ | +420 ± 30 +207 ± 17 (20 $\mu$M) +17 ± 3 (2 $\mu$m) | weak stimulation | IC$_{50}$ − 100 $\mu$M |
| 35 | H—CO$_2$—H$_2$CH=CH$_2$ | CH$_2$CH$_2$CH$_3$ | H$_2$CH$_2$CH$_3$ | +765 ± 61 +229 ± 14 (20 $\mu$M) +26 ± 5 (2 $\mu$M) | weak stimulation | IC$_{50}$ ~ 100 $\mu$M |
| | Diazepam | | | +150 to +300 (1 $\mu$M) | | |
| | $\alpha$-EMTBL | | | +152 ± 16 (1 mM) +20 − 50 (200 $\mu$M) 0 (100 $\mu$M) | 0 | IC$_{50}$ = 500 $\mu$m |

These examples of compounds and the results obtained with them are shown without implied limitation and illustrate the invention.

The conclusions which may be drawn from the activity-functional group study are as follows:

the most active compounds (that is to say, those producing the greater stimulation of the currents produced by GABA) are those simultaneously having gem-dialkyl substitution at the $\alpha$ (or 2) position and a secondary amide, a sulfonamide or a carbamate at the $\beta$ (or 3) position. The latter are represented respectively by the phenylcarboxamide 34 (420% stimulation of the currents produced by GABA at 200 $\mu$M; 207% stimulation at 20 $\mu$M; 17% stimulation at 2 $\mu$M), the p-chlorophenylsulfonamide 31 (23% stimulation at 5 $\mu$M (insoluble at higher concentrations)) and the allyl carbamate 35 (765% stimulation at 200 $\mu$M, 229% at 20 $\mu$M and 26% at 2 $\mu$M). The latter is the most active compound synthesized. In comparison, α-ethyl-α-methylthiobutyrolactone (α-EMTBL, 48), the most active anticonvulsant butyrolactone described to date, does not produce stimulation of the GABA currents at 100 μM. A concentration of α-EMTBL of 200 μM is required to produce a stimulation at 20% (G. C. Mathews et al., Neuropharmacology, 1996, 35, 123). The compounds of the present invention (for example 35) are therefore up to 100 times more powerful than α-EMTBL in stimulating the currents produced by GABA.

The importance of the simultaneous presence of the amine substituent in the β position and of the dialkyl substituents in the α position is demonstrated by the low stimulating activities for the GABA current of the compounds 26 (only an amine substituent on the lactone ring), 29 (only dialkyl substituents) and 28 (only an amine substituent and one alkyl substituent).

None of the compounds of the present invention displaces tritiated flunitrazepam from its binding site, thus indicating that these compounds do not bind to the benzodiazepine binding site of the GABA-A receptor. In some cases (for example, 31, 34, 35), weak stimulation of the binding of flunitrazepam is observed, probably due to allosteric interactions arising from the binding of these compounds to other sites on the receptor.

Weak interaction of some of these compounds (for example, 30, 31, 34, 35) with the picrotoxin binding site of the GABA-A receptor is demonstrated by the displacement of $S^{35}$-TBPS with $IC_{50}$ values of the order of 10 to 100 μM. There is no apparent correlation between the affinities with the TBPS binding site and the ability to stimulate the currents produced by GABA.

None of the compounds of the present invention displaces $H^3$-muscimol (table 1), thus indicating that these compounds do not bind to the GABA recognition site on the GABA-A receptor.

As is shown in table 3, the activity differs according to the stereochemistry of the amine substituent of the lactone ring. Thus, the compound R-30 (obtained either by separation of the racemic mixture on a chiral column or by enantiospecific synthesis starting from D-aspartic acid, scheme 4) is twice as powerful as the corresponding S isomer.

TABLE 3

Stimulation of the currents produced by
GABA by interaction of the enantiomers of the
compound 30 with the α1β2γ2 GABA-A recombinant
receptors

| Isomer | 100 μM | 10 μM |
|---|---|---|
| R-30 | +279 ± 94% | +51 ± 94% |
| S-30 | +104 ± 7% | +17 ± 5% |

While the compounds of the invention apparently do not interact with the benzodiazepine or GABA recognition sites of the GABA-A receptor and only bind weakly with the picrotoxin/TBPS recognition site, experiments with recombinant GABA-A receptors having different compositions of subunits suggest that at least some of the compounds can interact with the loreclezole binding site. Thus, it is observed that the compound R-30 (100 μM) produces a 5 times greater stimulation of the GABA currents in the receptors comprising the $β_2$ subunits with respect to the receptors carrying only the $β_1$ subunit (table 4). At 10 μM, the compound R-30 produces a stimulation only in the receptors comprising the $β_2$ subunit. The anticonvulsant loreclezole similarly enhances the activity of the GABA-A receptor by interacting with a site present on the receptors comprising the $β_2$ subunit (and the $β_3$ subunit) but not present on the receptors comprising the $β_1$ subunit (P. B. Wingrove, K. A. Wafford, C. Bain, P. J. Whiting, Proc. Natl. Acad. Sci. USA, 1994, 91, 4569). Furthermore, the anticonvulsant α-EMTBL is capable of stimulating the receptors comprising only the α subunits, suggesting that α-EMTBL does not act on the loreclezole binding site. The compounds of the present invention therefore appear to stimulate the activity of GABA by acting on a different site from that of α-EMTBL and related compounds, despite the apparent structural resemblance of these two classes of compounds.

TABLE 4

Stimulation of the currents produced by
GABA by the compound R-30 on GABA-A recombinant
receptors having a β1 or β2 subunits

| Subunits | 10 μM | 100 μM |
|---|---|---|
| α1β1 | −5 ± 11% | +92 ± 28% |
| α2β2 | +78 ± 4% | +588 ± 166% |

The following examples, given without implied limitation, illustrate the invention.

Process of Synthesis (R,S)-3-Benzylamino-1,4-butyrolactone 13

A solution of 2(5H)-furanone (2.5 g, 2.1 ml, 29.7 mmol) in methanol (3 ml) is cooled to 0° C. and treated with benzylamine (3.82 g, 3.9 ml, 35.7 mmol). The resulting solution is stirred at 0° C. for 24 hours. The solvent is evaporated and the residue is purified by flash chromatography (eluent 1/1: EtOAc/hexanes). The fractions comprising the substance with an Rf value of 0.07 are combined and concentrated to give the compound 13 in the form of a yellow oil (3.5 g, 60%).

Elemental analysis for $C_{11}H_{13}NO_2$: Calculated, %: C, 69.09; H, 6.85; N, 7.32. Found, %: C, 68.94; H, 6.82; N, 7.22.

General process for the alkylation of 3-benzylamino-1,4-butyrolactone [(R,S)-13]

A solution of lactone 13 in THF is added dropwise with stirring to a solution of lithium hexamethyldisilazide (2.2 equiv.) in THF at −78° C. under an argon atmosphere. After 30 minutes at this temperature, the electrophile in HMPA is then added via a hollow needle to the enolate solution. The mixture is then stirred for the specified time and the reaction is neutralized by addition of a saturated aqueous ammonium chloride solution. The mixture is then extracted several times with $CH_2Cl_2$ and the combined extracts are dried ($MgSO_4$), filtered and concentrated under reduced pressure. The crude products are then purified by chromatography, as will be described individually for each of them.

trans-3-Benzylamino-2-(C-methyl)-1,4-butyrolactone (trans-14)

A solution of lithium enolate, prepared from the lactone (R,S)-13 (0.366 g, 1.916 mmol), at −78° C. is treated with a solution of iodomethane (5 equiv., 0.6 ml, 9.58 mmol) in HMPA (0.5 ml). The resulting mixture and stirred at −78° C. for 2 hours. The reaction is then neutralized at 0° C. to produce a yellow oil. The crude product is purified by flash chromatography (1/1: EtOAc/hexanes). The fractions comprising the substance with an Rf value of 0.05 are combined and concentrated to produce 0.07 g (38%) of trans-14 ($R_1$=$CH_3$).

Elemental analysis for $C_{12}H_{15}NO_2$: Calculated, %: C, 70.22; H, 7.37; N, 6.82. Found, %: C, 70.04; H, 7.32; N, 6.79.

The fractions comprising the substance with an Rf value of 0.06 are combined and concentrated, so as to produce 0.016 g (9%) of cis-14 ($R_1$=$CH_3$).

cis- and trans-3-Benzylamino-2-(C-allyl)-1,4-butyrolactones cis-14 and trans-14, 3-Benzylamino-3,3-di (C-allyl)-1,4-butyrolactone 16

A solution of lithium enolate, prepared from the lactone (R,S)-13 (0.46 g, 2.44 mmol), at −78° C. is treated with a solution of allyl bromide (5 equiv., 1.16 ml, 12.2 mmol) in HMPA (5 ml). The resultant mixture is stirred at −78° C. for 2 hours. The reaction is then neutralized at 0° C. to produce a yellow oil. The crude product is purified by flash chromatography (1/1: EtOAc/hexanes). The fractions comprising the substance with an Rf value of 0.4 are combined and concentrated to produce 0.1 g (18%) of trans-14 ($R_1$=allyl).

HRMS, calculated for $C_{14}H_{18}NO_2$, gives 232.1337. 232.1337 was found. Infrared (film): 1772.5 (CO) cm$^{-1}$. Elemental analysis for $C_{14}H_{17}NO_2$: Calculated, %: C, 72.70; H, 7.41; N, 6.06. Found, %: C, 72.46; H, 7.61; N, 6.06.

The fractions comprising the substance with an Rf value of 0.5 are combined and concentrated to produce 0.015 g (9%) of cis-14 ($R_1$=allyl).

Infrared (film): 1772.3 (CO) cm$^{-1}$. MS (CI, Isobut.) m/z 232 (M+1). HRMS, calculated for $C_{14}H_{18}NO_2$: 232.1337. 232.1339 was found.

The fractions comprising the substance with an Rf value of 0.7 are combined and concentrated to produce the diallyl compound 16 (0.34 g, 52%).

MS (CI, Isobut.): m/z 272 (M+1). Infrared (film): 1639.3 (allyl), 1770 (lactone CO), 3338 (NH) cm$^{-1}$.

Elemental analysis for $C_{17}H_{21}NO_2$: Calculated, %: C, 75.25; H, 7.80; N, 5.16. Found, %: C, 74.87; H, 7.91; N, 5.08.

cis and trans-3-Benzylamino-2-(C-(p-methoxybenzyl))-1,4-butyrolactones cis-14 and trans-14

A solution of lithium enolate, prepared from the lactone (R,S)-13 (0.46 g, 2.44 mmol), at −78° C. is treated with a solution of p-methoxybenzyl bromide (5 equiv., 1.65 ml, 12.2 mmol) in HMPA (5 ml). The resulting mixture is stirred at −78° C. for 4 hours. The reaction is then neutralized at 0° C. to produce a yellow oil. The crude product is purified by flash chromatography (1/3: EtOAc/hexanes). The fractions comprising the substance with an Rf value of 0.2 are combined and concentrated to produce 0.076 g (10%) of trans-14 ($R_2$=p-methoxybenzyl).

Infrared (film): 1512.7, 1611.7, 1771.8 (lactone CO), 3400 (NH) cm$^{-1}$. MS (CI, isobut.): m/z 312 (M+1). HRMS, calculated for $C_{19}H_{22}NO_3$: 312.1599. 312.1595 was found.

The fractions comprising the substance with an Rf value of 0.3 are combined and concentrated to produce 0.05 g (7%) of cis-14 ($R_1$=p-methoxybenzyl).

Infrared (film): 1612.3, 1772.3 (lactone CO), 3398 (NH) cm$^{-1}$.

MS (CI, isobut.): m/z 312 (M+1). HRMS, calculated for $C_{19}H_{22}NO_3$: 312.1599. 312.1585 was found.

cis- and trans-3-Benzylamino-2-(C-(benzylethyl))-1,4-butyrolactones 38 and 39

A solution of lithium enolate, prepared from the lactone (R,S)-13 (0.11 g, 0.6 mmol), at −78° C. is treated with a solution of 2-bromoethylbenzene (5 equiv., 0.42 ml, 3 mmol) in HMPA (1 ml). The resulting mixture is stirred at −78° C. for 6 hours. The reaction is then neutralized at 0° C. to produce a yellow oil. The crude product is purified by flash chromatography (1/1: EtOAc/hexanes). The fractions comprising the substance with an Rf of 0.4 are combined and concentrated to produce the compound 39 (0.015 g, 8%).

MS (CI, Isobut.): mr/z 296 (M+1). HRMS, calculated for $C_{19}H_{22}NO_2$: 296.1650. 296.1650 was found.

The fractions comprising the substance with an Rf of 0.5 are combined and concentrated to produce the compound 38 (0.01 g, 6%).

MS (CI, Isobut.): m/z 296 (M+1). HRMS, calculated for $C_{19}H_{22}NO_2$: 296.1650. 296.1658 was found.

General Procedure for the Preparation of 3-benzyloxy-carbonylamino-1,4-butyrolactones A solution of lactones (R,S)-14 or 15 (1.63 mmol) in ethanol (10 ml) comprising palladium-on-carbon (10%) is stirred under hydrogen (40 psi) for 16 hours. The mixture is filtered, the solvent is evaporated from the filtrate and the residue is used in the following stage without further purification. Benzyl chloroformate (1.2 equiv.) is added at 0° C. to the resulting mixture comprising the 4-aminolactones, $CH_2Cl_2$ (3 ml), $Et_3N$ (0.4 ml) and DMAP (0.045 g), and the reaction mixture is stirred at this temperature for 30 minutes. After 12 hours at ambient temperature, the solvent is removed under reduced pressure and the residue is purified by flash chromatography.

The cis- and trans-3-benzyloxycarbonylamino-2-(C-methyl)-1,4-butyrolactones 27 and 28 are prepared as described above from the compound 14 ($R_1$=$CH_3$). The products are chromatographed on silica gel, using EtOac/hexanes (1/1) as eluent. The fractions comprising the substance with an Rf value of 0.4 are combined and concentrated to produce the compound 28 (27%), the melting point of which is 127–128° C.

MS (CI, Isobut.): m/z 250 (M+1). HRMS, calculated for $C_{13}H_{15}NO_4$: 249.1000. 249.0978 was found.

The fractions comprising the substance with an Rf value of 0.5 are combined and concentrated to produce the compound 27(15%).

MS (FAB, Thioglycerol): m/z 248 (M−1). HRMS, calculated for $C_{13}H_{15}NO_4$: 249.1000. 249.0992 was found.

3-Benzyloxycarbonylamino-2,2-(C-dipropyl)-1,4-butyrolactone 30 is prepared as described above from the compound 16. The product is chromatographed on silica gel, using EtOAc/hexanes (1/1) as eluent. The fractions comprising the substance with an Rf value of 0.7 are combined and concentrated to produce the compound 30 in the form of a white solid (52%) having a boiling point of 91–92° C.

MS (CI, Isobut.): m/z 320 (M+1). Infrared (KBr): 1556.7, 1684–1698 (O—CO—N), 1774.1 (lactone CO) cm$^{-1}$.

Elemental analysis for $C_{18}H_{25}NO_4$: Calculated, %: C, 67.69; H, 7.89; N, 4.39. Found, %: C, 67.94; H, 7.84; N, 4.25.

3-Benzyloxycarbonylamino-1,4-butyrolactone 26 is prepared as described above from the compound 13. The product is chromatographed on silica gel, using EtOAc/hexanes (1/1) as eluent. The fractions comprising the substance with an Rf value of 0.4 are combined and concentrated to produce the compound 26 in the form of a white solid (61%) having a melting point of 101–102° C.

MS (CI, Isobut.): m z 236 (M+1). Infrared (KBr)c: 1552, 1673–1693 (O—CO—N), 1779.4 (lactone CO), 3307.7

(NH) cm$^{-1}$. Elemental analysis for $C_{12}H_{13}N_2O_4$: Calculated, %: C, 61.27; H, 5.57; N, 5.95. Found %: C, 61.39; H, 5.66; N, 5.91.

General Process for the Preparation of 3-(N-benzyl-N-benzyloxycarbonyl)amino-1,4-butyrolactones Benzyl chloroformate (1.2 equiv.) is added at 0° C. to a mixture of 3-benzylamino-2-(C-methyl)-1,4-lactone 14 (1.63 mmol), Et$_3$N (0.4 ml) and DMAP (0.045 g) in CH$_2$Cl$_2$ (5 ml). After 30 minutes at 0° C. and then 12 hours at ambient temperature, the solvent is removed under reduced pressure and the residue is purified by flash chromatography.

The cis and trans-3-(N-benzyl-N-benzyloxycarboyl)amino-2-(C-methyl)-1,4-butyrolactones 43 and 42 are prepared as described above from the compound 14 ($R_1$=CH$_3$). The products are chromatographed on silica gel, using EtOAc/hexanes (1/1) as eluent. The fractions comprising the substance with an Rf value of 0.6 are combined and concentrated to produce the compound 43 (11%).

Elemental analysis for $C_{20}H_{21}NO_4$: Calculated, %: C, 68.55; H, 6.71. Found, %: C, 68.18; H, 6.56.

The fractions comprising the substance with an Rf value of 0.7 are combined and concentrated to produce the compound 42 (22%).

Elemental analysis for $C_2OH_{21}NO_4$: Calculated, %: C, 68.55; H, 6.71. Found, %: C, 68.42; H, 6.38.

N-(Benzyloxycarbonyl)-D-aspartic anhydride (25) is prepared from N-(benzyloxycarbonyl)-D-aspartic acid (24) by the method of McGarvey et al. (G. J. McGarvey et al., J. Amer. Chem. Soc., 1986, 108, 4943) with an overall yield of 80% with respect to D-aspartic acid (D-23). The melting point is 126–127° C. $[\alpha]_D$+26° (c 1.22, MeOH). Infrared (KBr): 1529, 1697 (O—CO—N), 1781 and 1866 (anhydride).

3-(R)-[Benzyloxycarbonyl)amino]-1,4-butyrolactone (R)-26

0.9 g (3.6 mmol) of anhydride 25 in THF (8 ml) is added dropwise to a stirred slurry of 0.138 g (3.6 mmol) of sodium borohydride in THF (7 ml) at 0° C. After stirring at ambient temperature for 1 hour, the reaction mixture is carefully acidified to pH 2 with 6N HCl and is then concentrated to approximately a quarter of its volume under reduced pressure (water suction). The residue is diluted with water and extracted with 4 portions of ethyl acetate and then the combined organic extracts are concentrated under reduced pressure. The crude product is purified by flash chromatography (1/1: EtOAc/hexanes). The fractions comprising the substance with an Rf value of 0.4 are combined and concentrated to produce the compound (R)-26 in the form of a white solid (50%) having a melting point of 101–102° C. $[\alpha]_D$+49.2° (c 1, CHCl$_3$). MS (CI, Isobut.): m/z 236 (M+1). Infrared (KBr): 1558, 1674–1694 (O—CO—N), 1780 (lactone CO), 3307.4 (NH) cm$^{-1}$.

3-(R)-Benzylamino-1,4-butyrolactone (R)-13

A solution of 0.15 g of lactone (R)-26 (0.64 mmol) in EtOAc (10 ml) comprising palladium-on-carbon (10%) is stirred under hydrogen (30 psi) at ambient temperature for 4 hours. The mixture is filtered, the solvent is evaporated from the filtrate and the residue is used in the following stage without further purification. 0.065 ml (0.64 mmol) of benzaldehyde is added with cooling to the resulting mixture comprising the 3-aminolactone in methanol (3 ml). After having left the solution standing for 1 hour, it is diluted with methanol, to produce a total volume of 20 ml, and hydrogenated with a platinum oxide catalyst under a pressure of 40 psi. The reduction is completed in three hours. After having removed the catalyst, the solvent is evaporated and the residue is purified by flash chromatography (1/1: EtOAc/hexanes). The fractions comprising the substance with an Rf value of 0.07 are combined and concentrated to produce the compound (R)-13 in the form of a colorless oil (0.07 g, 57%).

$[\alpha]_D$+16.5° C. (C 1, CHCl$_3$). H$^1$ NMR (200 MHz, CDCl$_3$) δ: 1.62 (1H, s, NH), 2.38 (1H, dd, $J_1$=17.5 Hz, $J_2$=4.6 Hz), 2.70 (1H, dd, $J_1$, $J_3$=7.1 Hz), 3.67 (1H, m), 3.79 (2H, s), 4.11 (1H, dd, $J_4$=9.5 Hz, $J_5$=3.9 Hz), 4.36 (1H, dd, $J_4$, $J_5$=5.9 Hz), 7.26–7.37 (5H, m).

3-(R)-Benzylamino-2,2-di(C-allyl)-1,4-butyrolactone (R-16) is synthesized in the way described above for the compound R,S-16. Briefly, a solution of lithium enolate, prepared from the lactone (R)-13 (0.092 g, 0.488 mmol), at −78° C. is treated with a solution of allyl bromide (5 equiv., 0.23 ml, 2.44 mmol) in HMPA (1 ml). The resulting mixture is stirred at −78° C. for 2 hours. The reaction is then neutralized at 0° C. to produce a yellow oil. The crude product is purified by flash chromatography (1/1: EtOAc/hexanes). The fractions comprising the substance with an Rf value of 0.4 are combined and concentrated to produce the monoallyl derivative (0.01 g, 9%).

$[\alpha]_D$+32.6° (c 1, CHCl$_3$). H$^1$ NMR (300 MHz, CDCl$_3$) δ: 1.64 (1H, NH), 2.24 (1H, m), 2.39 (2H, m), 2.60 (1H, m), 3.75 (2H, q, $J_1$=12.1 Hz), 4.23 (1H, dd, $J_2$=9.03 Hz, $J_3$=6.41 Hz), 4.36 (1H, dd, $J_2$, $J_4$=6.64 Hz), 5.24 (2H, m), 5.85 (1H, m), 7.31–7.35 (5H, m).

The fractions comprising the substance with an Rf value of 0.7 are combined and concentrated to produce the diallyl compound R-16 (0.068 g, 52%).

$[\alpha]_D$+1.4° (c 0.8, CHCl$_3$). H$^1$ NMR (300 MHz, CDCl$_3$) δ: 1.51 (1H, NH), 2.32 (2H, m), 2.47 (2H, m), 3.54 (1H, dd, $J_1$=8.43 Hz, $J_2$=7.68 Hz), 3.80 (2H, s), 3.81 (1H, dd, $J_3$=17.55 Hz, $J_4$=6.4 Hz), 4.28 (1H, dd, $J_3$, $J_5$=7.68 Hz), 5.00–5.22 (4H, m), 5.68 (1H, m), 5.88 (1H, m), 7.30–7.36 (5H, m).

3-(R)-Benzyloxycarbonylamino-3,3-di(C-propyl)-1,4-butyrolactone (R-30) is prepared from the compound R-16 as defined above for the compound R,S-30. The product is chromatographed on silica gel, using EtOAc/hexanes (1/1) as eluent. The fractions comprising the substance with an Rf value of 0.7 are combined and concentrated to produce the compound R-30 in the form of a colorless oil (57%).

$[\alpha]_D$−0.28° C. (c 1.44, CHCl$_3$). H$^1$ NMR (250 MHz, CDCl$_3$) δ: 0.90 (3H, t, $J_1$=7.2 Hz), 0.92 (3H, t, $J_2$=7.1 Hz), 1.18–1.69 (8H, m), 3.84 (1H, dd, $J_3$=8.6 Hz, $J_4$=7.4 Hz), 4.45–4.58 (2H, m), 4.88 (1H, NH, d, $J_5$=8.28 Hz), 5.12 (2H, s), 7.36 (5H, s).

This product is identical by HPLC analysis (retention time: 12.3 min) to the substance obtained from the analytical HPLC separations of the racemic mixture (eluent 9/1: hexane/isopropanol) on a chiral OD column.

General Process for the Preparation of the 3-sulfonyl-and -acylamino-2,2-di(C-propyl)-1,4-butyrolactones 31–36

A solution of lactone R,S-16 (1.63 mmol) in ethanol (10 ml) comprising palladium-on-carbon (10%) is stirred under hydrogen (40 psi) for 16 hours. The mixture is filtered, the solvent is evaporated from the filtrate and the residue is used in the following stage without further purification. R-Cl (1.2 equiv.) is added at 0° C. to the resulting mixture comprising 3-amino-2,2-dipropylbutyrolactone, CH$_2$Cl$_2$ (3 ml), Et$_3$N (0.4 ml) and DMAP (0.045 g), and the reaction mixture is stirred at this temperature for 30 minutes. After 12 hours at ambient temperature, the solvent is removed under reduced pressure and the residue is purified by flash chromatography.

3-(p-Chlorophenylsulfonamido)-2,2-di(C-propyl)-1,4-butyrolactone 31 is prepared from the compound 16 and p-chlorophenylsulfonyl chloride in the way described above. The product is chromatographed on silica gel, using EtOAc/hexanes (1/1) as eluent. The fractions comprising the substance with an Rf value of 0.7 are combined and concentrated to produce the compound 31 in the form of a white solid (84%) having a melting point of 96–97° C.

MS (CI, Isobut.): m/z 360 (M+1). Infrared (KBr): 1173.7 and 1477.7 ($SO_2N$—), 1757.7 (lactone CO) $cm^{-1}$. Elemental analysis for $C_{16}H_{22}NO_4SCl+0.1hexane$: Calculated, %: C, 54.11; H, 6.40; N, 3.80; S, 8.70. Found, %: C, 54.22; H, 6.19; N, 3.57; S, 8.65.

3-(p-Trifluoromethylphenylsulfonamido)-2,2-di(C-propyl)-1,4-butyrolactone 32 is prepared in the way described above from the compound 16 and p-trifluoromethylphenyl-sulfonyl chloride. The product is chromatographed on silica gel, using EtOAc/hexanes (1/1) as eluent. The fractions comprising the substance with an Rf value of 0.6 are combined and concentrated to produce the compound 32 in the form of a white solid (57%) having a melting point of 106–107° C.

MS (CI, Isobut.): m/z 394 (M+1). Infrared (KBr): 1168.9 and 1323.3 ($SO_2N$—), 1752.9 (lactone CO) $cm^{-1}$. Elemental analysis for $C_{17}H_{22}NO_4SF_3+0.1H_2O$: Calculated, %: C, 51.66; H, 5.66; N, 3.54; S, 8.11. Found, %: C, 51.27; H, 5.31; N, 3.32; S, 8.42.

3-(p-Methoxyphenylsulfonamido)-2,2-di(C-propyl)-1,4-butyrolactone 33 is prepared in the way described above from the compound 16 and p-methoxyphenylsulfonyl chloride. The product is chromatographed on silica gel, using EtOAc/hexanes (1/1) as eluent. The fractions comprising the substance with an Rf value of 0.6 are combined and concentrated to produce the compound 33 in the form of a white solid (84%) having a melting point of 103–104° C.

MS (CI, Isobut.): m/z 356 (M+1). Infrared (KBr): 1167.8 and 1323.3 ($SO_2N$—), 1753.7 (lactone CO) $cm^{-1}$. Elemental analysis for $C_{17}H_{25}NO_5S+0.1hexane$: Calculated, %: C, 58.06; H, 7.31; N, 3.85; S, 8.81. Found, %: C, 58.28; H, 7.21; N, 3.96; S, 8.46.

3-Benzylamino-2,2-di(C-propyl)-2,4-butyrolactone 34 is prepared in the way described above from the compound 16 and benzoyl chloride. The product is chromatographed on silica gel, using EtOAc/hexanes (1/1) as eluent. The fractions comprising the substance with an Rf value of 0.5 are combined and concentrated to produce the compound 34 in the form of a white solid (57%) having a melting point of 130–131° C.

MS (CI, Isobut.): m/z 290 (M+1). Infrared (KBr): 1546.8, 1637.1 (CO—N), 1766.69 (lactone CO), 3306.4 (NH) $cm^{-1}$. Elemental analysis for $C_{17}H_{23}NO_3$: Calculated, %: C, 70.56; H, 8.01; N, 4.84. Found, %: C, 70.37; H, 7.91; N, 4.75.

3-Allyloxycarbonylamino-2,2-di(C-propyl)-1,4-butyrolactone 35 is prepared in the way described above from the compound 16 and allyloxycarbonyl chloride. The product is chromatographed on silica gel, using EtOAc/heptanes (1/1) as eluent. The fractions comprising the substance with an Rf value of 0.6 are combined and concentrated to produce the compound 35 in the form of a white solid (81%) having a melting point of 80–81° C.

MS (CI, Isobut.): m/z 270 (M+1). Infrared (KBr): 1557.2, 1686.1 (O—CO—N), 1777.4 (lactone CO), 3315.9 (NH) $cm^{-1}$. Elemental analysis for $C_{14}H_{23}NO_4$: Calculated, %: C, 62.43; H, 8.61; N, 5.20. Found, %: C, 62.41; H, 8.49; N, 5.09.

3-Ethyloxycarbonylamino-2,2-di(C-propyl)-1,4-butyrolactone 36 is prepared in the way described above from the compound 16 and ethyloxycarbonyl chloride. The product is chromatographed on silica gel, using EtOAc/heptanes (1/1) as eluent. The fractions comprising the substance with an Rf value of 0.5 are combined and concentrated to produce the compound 36 in the form of a white solid (77%) having a melting point of 111–112° C.

MS (CI, Isobut.): m/z 258 (M+1). Infrared (KBr): 1548.39, 1690.1 (O—CO—N), 1787.8 (lactone CO), 3326.2 (NH) $cm^{-1}$. Elemental analysis for $C_{13}H_{23}NO_4$: Calculated, %: C, 60.68; H, 9.01; N, 5.44. Found, %: C, 60.67; H, 8.86; N, 5.43.

3-tert-Butyloxycarbonylamino-2,2-di(C-propyl)-1,4-butyrolactone 37 is prepared in the way described above from the compound 16 and di-tert-butyl dicarbonate. The product is chromatographed on silica gel, using EtOAc/heptanes (1/1) as eluent. The fractions comprising the substance with an Rf value of 0.7 are combined and concentrated to produce the compound 37 in the form of a white solid (70%) having a melting point of 134–135° C.

MS (EI, MeOH): m/z 285 (M). Infrared (KBr): 1683.3 (O—CO—N), 1768.6 (lactone CO), 3340.2 (NH) $cm^{-1}$.

Elemental analysis for $C_{15}H_{27}NO_4$: Calculated, %: C, 63.13; H, 9.54; N, 4.91. Found, %: C, 63.33; H, 9.48; N, 4.89.

3-[p-Aminophenylsulfonamido]-2,2-di(C-propyl)-1,4-butyrolactone 44 is prepared in the way described above from the compound 16 and p-nitrophenylsulfonyl chloride. The product is chromatographed on silica gel, using EtOAc/heptanes (1/1) as eluent. The fractions comprising the substance with an Rf value of 0.6 are combined and concentrated to produce 3-[p-nitro-phenylsulfonamido]-2,2-di(C-propyl)-1,4-butyrolactone (94%). The latter is reduced by catalytic hydrogenation in the way described above to produce the compound 44 (Rf=0.3, 87%).

MS (EI, MeOH): m/z 340 (M). Elemental analysis for $C_{16}H_{24}N_2O_4S+0.5H_2O$: Calculated, %: C, 54.99; H, 7.21; N, 7.02, S, 9.17. Found, %: C, 55.11; H, 6.88; N, 6.96; S, 9.03.

3-[p-(Allyloxycarbonylamino)phenylsulfonamido]-2,2-di(C-propyl)-1,4-butyrolactone 45 is prepared in the way described above from the compound 44 and allyl chloroformate. The product is chromatographed on silica gel, using EtOAc/heptanes (1/1) as eluent. The fractions comprising the substance with an Rf value of 0.5 are combined and concentrated to produce the hygroscopic compound 45 (77%).

MS (EI, MeOH): m/z 424 (M). Elemental analysis for $C_{20}H_{28}N_2O_6S+0.1C_7H_{16}$: Calculated, %: C, 57.22; H, 6.87; N, 6.15. Found, %: C, 57.08; H, 6.81; N, 5.94.

What is claimed is:
1. A compound represented by the following general formula:

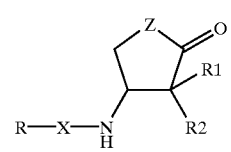

in which:
Z represents a sulfur or oxygen atom,
the R1 and R2 groups, which can be identical to or different from one another, each represent an alkyl group or an alkenyl group, X represents a CO, a $CO_2$, an SO or an $SO_2$, and the R group represents an alkyl, aryl, alkenyl or aralkyl group, provided that, when Z represents an oxygen atom, X an $SO_2$ and R a

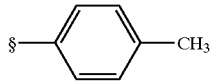

group,

R1 and R2 do not both represent the methyl group.

2. The compound as claimed in claim 1, wherein Z represents an oxygen atom.

3. The compound as claimed in claim 2, wherein it is represented by the general formula:

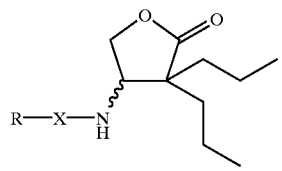

in which:

X represents a CO, a $CO_2$, an SO or an $SO_2$, and the R group represents an alkyl, aryl, alkenyl or aralkyl group.

4. The compound as claimed in claims 1 to 3, wherein it is represented by the formula:

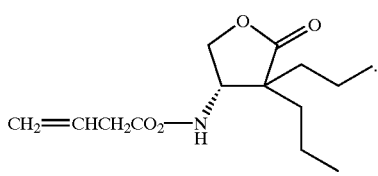

5. A process for the preparation of the compound of following general formula I:

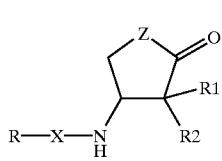

I in which:

Z represents a sulfur or oxygen atom, the R1 and R2 groups, which can be identical to or different from one another, each represent an alkyl group or an alkenyl group, X represents a CO, a $CO_2$, an SO or an $SO_2$, and the R group represents an alkyl, aryl, alkenyl or aralkyl group, characterized in that the amine of the compound of general formula:

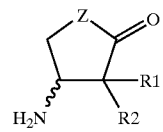

in which:

Z represents a sulfur or oxygen atom, and the R1 and R2 groups, which can be identical to or different from one another, each represent an alkyl group or an alkenyl group, is treated with an appropriate reactant to produce the compounds of general formula I.

6. The preparation process as claimed in claim 5, further comprising a preliminary hydrogenolysis stage to remove the benzyl group from the compound of general formula:

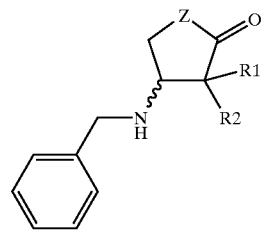

in which:

Z represents a sulfur or oxygen atom, and the R1 and R2 groups, which can be identical to or different from one another, each represent an alkyl group or an alkenyl group.

7. The preparation process as claimed in claim 6, further comprising a preliminary stage of alkylation in the C-2 position of the compound of general formula:

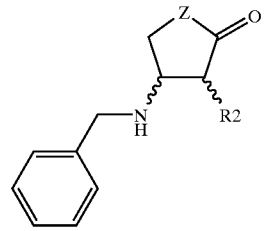

in which:

Z represents a sulfur or oxygen atom, and the R1 group represents an alkyl group or an alkenyl group, by treatment with a strong base, followed by the addition of an alkylating agent of general formula R2X in which R2 represents an alkyl, alkenyl or aralkyl group.

8. The preparation process as claimed in claim 7, further comprising a preliminary stage of monoalkylation in the C-2 position of the 3-benzylaminolactone of general formula:

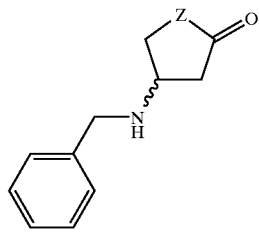

in which:

Z represents a sulfur or oxygen atom, by treatment with a strong base, followed by the addition of an alkylating agent of general formula R1X in which R1 represents an alkyl, alkenyl or aralkyl group.

9. The preparation process as claimed in claim 8, further comprising a preliminary stage of 1,4 addition of Michael type of benzylamine to an unsaturated 1,4-butyrolactone or 1,4-thiobutyrolactone to give the corresponding 3-benzylaminolactone.

10. The preparation process as claimed in claim 9, wherein D- or L-aspertic acid is used as a starting material in a first stage to produce any one of the compounds as claimed in claims 1 to 3 in optically pure form.

11. The preparation process as claimed in claims 7 to 10, wherein the strong base used to carry out the alkylations is lithium hexamethyldisilazide.

12. The preparation process as claimed in claim 5, wherein the reactant is one of the family of the acyl chlorides, sulfonyl chlorides or chloroformates.

13. A pharmaceutical composition comprising a compound of following general formula:

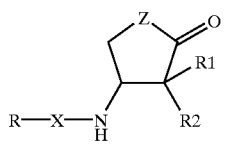

in which:

Z represents a sulfur or oxygen atom, the R1 and R2 groups, which can be identical to or different from one another, each represent an alkyl group or an alkenyl group, X represents a CO, a $CO_2$, an SO or an $SO_2$, and the R group represents an alkyl, aryl, alkenyl or aralkyl group, and an appropriate pharmaceutical carrier.

14. Method of using of the compounds of following general formula:

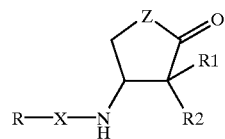

as stimulant of the activity of Y-aminobutyric acid acting via GABA-A receptor of the central nervous system in which:

Z represents a sulfur or oxygen atom, the R1 and R2 groups, which can be identical to or different from one another, each represent an alkyl group or an alkenyl group, X represents a CO, a $CO_2$, an SO or an $SO_2$, and the R group represents an alkyl, aryl, alkenyl or aralkyl group.

15. A medicament comprising a compound of following general formula:

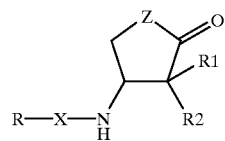

in which:

Z represents a sulfur or oxygen atom, the R1 and R2 groups, which can be identical to or different from one another, each represent an alkyl group or an alkenyl group, X represents a CO, a $CO_2$, an SO or an $SO_2$, and the R group represents an alkyl, aryl, alkenyl or aralkyl group.

16. Method of using the compounds of following general formula for the treatment of nervous disorders:

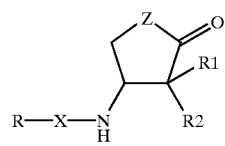

for the treatment of nervous disorders in which:

Z represents a sulfur or oxygen atom, the R1 and R2 groups, which can be identical to or different from one another, each represent an alkyl group or an alkenyl group, X represents a CO, a $CO_2$, an SO or an $SO_2$, and the R group represents an alkyl, aryl, alkenyl or aralkyl group.

17. The use as claimed in claim 16, wherein the nervous disorders are of the following types: epilepsy, anxiety, depression, sleep disorders, panic attacks, muscular contractions, pain, dependence on alcohol or benzodiazepines, or psychotic behaviors.

* * * * *

UNITED STATES PATENT AND TRADEMARK OFFICE
CERTIFICATE OF CORRECTION

PATENT NO. : 6,660,769 B1
DATED : December 9, 2003
INVENTOR(S) : Robert Dodd et al.

It is certified that error appears in the above-identified patent and that said Letters Patent is hereby corrected as shown below:

Column 11,
Line 32, please add -- 15 -- after "dialkylated derivatives".

Columns 11 and 12,
Concerning scheme 2, last line, change "CO-alkeny" to -- CO-alkenyl --.

Column 14,
Line 2, please change "$[\alpha]_D = 0.28$ CHCl$_3$))" to -- $[\alpha]_D = -0.28$ CHCl$_3$)) --.

Columns 19 and 20,
Table 1c - first line - row R, please change "NH-CO-OCH$_2$-H=CH$_3$" to -- NH-CO-OCH$_2$-H=CH$_2$ --.

Column 32,
Lines 45-55, the formula is wrong, it must be replaced with the one below:

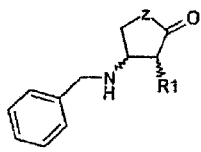

Column 34,
Line 34, please delete "for the treatment of nervous disorders"

Signed and Sealed this

Twenty-fourth Day of August, 2004

JON W. DUDAS
*Director of the United States Patent and Trademark Office*